United States Patent
Sloman et al.

(10) Patent No.: US 8,386,033 B2
(45) Date of Patent: Feb. 26, 2013

(54) FREQUENCY DOMAIN ANALYSIS TO DETECT T WAVE OVERSENSING

(75) Inventors: Laurence S. Sloman, West Hollywood, CA (US); Stuart Rosenberg, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 565 days.

(21) Appl. No.: 12/607,847

(22) Filed: Oct. 28, 2009

(65) Prior Publication Data

US 2011/0098764 A1    Apr. 28, 2011

(51) Int. Cl.
*A61N 1/39* (2006.01)
(52) U.S. Cl. ............... 607/5; 600/508; 600/509
(58) Field of Classification Search .......... 600/508–509, 600/521
See application file for complete search history.

(56) References Cited

U.S. PATENT DOCUMENTS

| 7,141,017 | B2 | 11/2006 | Laske et al. |
| 7,813,791 | B1* | 10/2010 | Gill et al. ............ 600/521 |
| 2007/0265508 | A1 | 11/2007 | Sheikhzadeh-Nadjar et al. |
| 2008/0109041 | A1 | 5/2008 | de Voir |

* cited by examiner

*Primary Examiner* — Carl H Layno
*Assistant Examiner* — Paula J Stice

(57) ABSTRACT

Detection of T wave oversensing in an ICD is accomplished in order to prevent improper application of treatment to a patient. The ICD device senses for electrical impulses representing the R waves of a beating heart. In some instances the ICD device will sense T waves that it will assume to be R waves, because the ICD device expects or assumes that such sensed signals are R waves. Time intervals between each detected, assumed R waves are measured and a list of intervals is generated. The list is transformed into its frequency domain equivalent and analyzed for peaks and randomness criteria to determine whether T wave oversensing has occurred.

18 Claims, 10 Drawing Sheets

FREQUENCY DOMAIN ANALYSIS TO DETECT T WAVE OVERSENSING

FIELD OF THE DISCLOSURE

The present disclosure relates, in general, to medical devices, and, more particularly, to frequency domain analysis to detect T wave oversensing.

BACKGROUND

An implantable cardioverter defibrillator (ICD) is a small battery-powered electrical impulse generator that is typically implanted in persons who are at risk of sudden cardiac death due to ventricular fibrillation. ICDs are generally programmed to detect cardiac arrhythmia and correct it by delivering a treatment of electricity to the appropriate location in the person's heart. ICDs monitor the rate and rhythm of the heart and deliver such electrical therapies when the electrical properties of the heart activity present some pre-defined variance from the norm.

FIG. 3 is an illustration of a typical electrocardiograph (ECG) trace 300 over a single cardiac cycle 35. The ECG trace 300 presents several negative and positive deflections that correspond to the different electrical sequences that a heart goes through during a typical heartbeat, such as cardiac cycle 35. During normal atrial depolarization, the primary electrical impulse is directed from the sino-atrial (SA) node, i.e., the heart's pacemaker, toward the atrial-ventricular (AV) node. It will then spread from the right atrium to the left atrium. The path of this primary electrical impulse results in a P wave deflection 301 in the ECG trace 300.

After filling with blood resulting from the atrial depolarization, the ventricles also depolarize to pump the blood into the aorta for distribution to the body and the pulmonary arteries for distribution to the lungs. This ventricular depolarization ideally results in a quick succession of wave deflections in the ECG trace 300: a Q wave deflection 302, an R wave deflection 303, and an S wave deflection 304. The collection of the Q wave deflection 302, R wave deflection 303, and S wave deflection 304, representing the ventricular depolarization in ECG trace 300, is referred to as the QRS complex 305. The illustrated QRS complex 305 represents an idealized deflection formation for a typical heartbeat, such as cardiac cycle 35. However, a normal heartbeat may not always present with all three waves of the QRS complex 305. Generally, any combination of presenting Q, R, or S waves will be referred to as the QRS complex 305.

Because the ventricles contain more muscle mass than the atria, the QRS complex 305 is much larger than the P wave deflection 301. The shape of the QRS complex 305 will typically change when there is an abnormal conduction of the electrical impulses within the ventricles. However, the shape of the QRS complex 305 may also change depending on which recording electrodes of the ECG detect the electrical impulses.

After pumping the blood from the ventricles through depolarization, the ventricles repolarize during which time the atria relax and refill with blood for the next heartbeat. The repolarization of the ventricles presents as a T wave deflection 306 in the ECG trace 300. The collection of the P wave deflection 301, the QRS complex 305, and the T wave deflection 306 represents the typical heartbeat in the ECG trace 300. A fourth section, which is not always reflected or measured in an ECG trace, such as ECG trace 300, is a U wave deflection 307. The U wave deflection 307 is thought to represent the repolarization of the papillary muscles or His/Purkinje fibers, which are part of the system that coordinates the depolarization of the ventricles.

The illustration of the ECG trace 300 represents an idealized shape of an ECG trace of a normal heartbeat. In practice, ECG traces may present quite differently from the idealized shape of the ECG trace 300. These different shapes may be due to many different factors which include not only heart abnormalities, but also include the mere position of the patient being measured (e.g., prone vs. supine) or a physiologic problem caused by a drug interaction or activity of the patient. ICDs generally include filters that filter out the P, Q, S, and T waves. Thus, the ICD expects to only detect the R wave deflection. However, if one of these external factors causes the T wave deflection amplitude to increase over the filter limits, the ICD will sense the T wave deflection (i.e., oversensing) which the ICD expects to be indicative of an R wave deflection. The ICD is programmed to interpret this particular quick succession of R wave deflections as ventricular tachycardia, which if accurately detected, could be a precursor condition to ventricular fibrillation. Therefore, the ICD will attempt to treat the condition to prevent the heart from going into ventricular fibrillation. In the situation where the ICD over senses the T wave deflection when ventricular tachycardia is not present, an inappropriate electrical therapy may be delivered to the patient. The delivery of electrical therapy to the patient when the patient is not in cardiac distress can be quite uncomfortable. Thus, it is desirable to reduce or eliminate false positives.

ICD manufacturers have attempted to minimize the oversensing problem by adding automatic sensing control (ASC). One method employed in an ASC is bigeminal avoidance. Bigeminy is a slightly abnormal heart arrhythmia that presents as a normal sinus heartbeat with a premature ventricular beat. Various algorithms analyze beat intervals to predict that a bigeminal beat pattern is not, in fact, a tachycardial episode that merits treatment. These bigeminal avoidance techniques generally work when the bigeminy is experienced on every single beat. However, when the bigeminal beat is not experienced on every beat, these avoidance techniques do not consistently prevent improper treatment. Moreover, additional algorithms used in ASC systems include timing parameters, such that if a patient experiences a high rate for more than a predefined period of time, treatment will be administered, even if this detected high rate is due to detection of the bigeminal beat. Therefore, even the methods in ASC systems to avoid improper administration of treatment do not always prevent such improper treatment.

SUMMARY

The various embodiments of the present teachings are directed to detection of T wave oversensing in an ICD device to prevent improper application of treatment to a patient. The ICD device senses for electrical impulses representing the R waves of a beating heart. Because the ICD device only expects to sense R waves, any T waves that may be over sensed will show up or be assumed by the ICD device as additional R waves. Time intervals between each detected, assumed R wave are measured and a list of intervals is generated. The list is transformed into its frequency domain equivalent and analyzed to determine whether T wave oversensing has occurred.

Representative embodiments of the present teachings are directed to methods for determining T wave oversensing in cardiac electrical signals. These methods include receiving a list of assumed R-R intervals for a beating heart, transforming this list of intervals into its frequency domain equivalent responsive to the list indicating a tachyarrhythmia, and analyzing the frequency domain equivalent to determine that the list includes over sensed T waves.

Additional representative embodiments of the present teachings are directed to ICD devices that include cardiac sensors configured to sense electrical impulses emitted from a beating heart, shocking terminals configured to apply stimulation therapy to the beating heart in response to detecting a treatable arrhythmia, a programmable microcontroller coupled to the cardiac sensors and to the shocking terminals, wherein the programmable microcontroller controls operation of the ICD device, and a memory coupled to the programmable microcontroller. An arrhythmia detection module is stored in the memory. When it is executed by the programmable microcontroller, the arrhythmia detection module configures the ICD device to detect a tachyarrhythmia from a list of assumed R-R intervals measured from the beating heart. A T wave oversensing detector module is also stored in the memory. When executed by the programmable microcontroller, the T wave oversensing detector module further configures the ICD device to transform the list of assumed R-R intervals into its frequency domain equivalent, analyze the frequency domain equivalent to detect T wave oversensing, and block the shocking terminals from applying stimulation therapy based on the detected T wave oversensing.

Further representative embodiments of the present teachings are directed to systems for detecting T wave oversensing in cardiac electrical signals. These systems include means for receiving a list of assumed R-R intervals for a beating heart, means, operable responsive to the list of intervals indicating a tachyarrhythmia, for transforming the list into its frequency domain equivalent, and means for analyzing the frequency domain equivalent to determine that the list includes over sensed T waves.

The foregoing has outlined rather broadly the features and technical advantages of the present teachings in order that the detailed description of the teachings that follows may be better understood. Additional features and advantages of the teachings will be described hereinafter which form the subject of the claims of the teachings. It should be appreciated by those skilled in the art that the conception and specific embodiment disclosed may be readily utilized as a basis for modifying or designing other structures for carrying out the same purposes of the present teachings. It should also be realized by those skilled in the art that such equivalent constructions do not depart from the spirit and scope of the teachings as set forth in the appended claims. The novel features which are believed to be characteristic of the teachings, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present teachings.

BRIEF DESCRIPTION OF THE DRAWINGS

For a more complete understanding of the present disclosure, reference is now made to the following descriptions taken in conjunction with the accompanying drawings.

DETAILED DESCRIPTION

Overview of Implantable Devices

Figure 1:
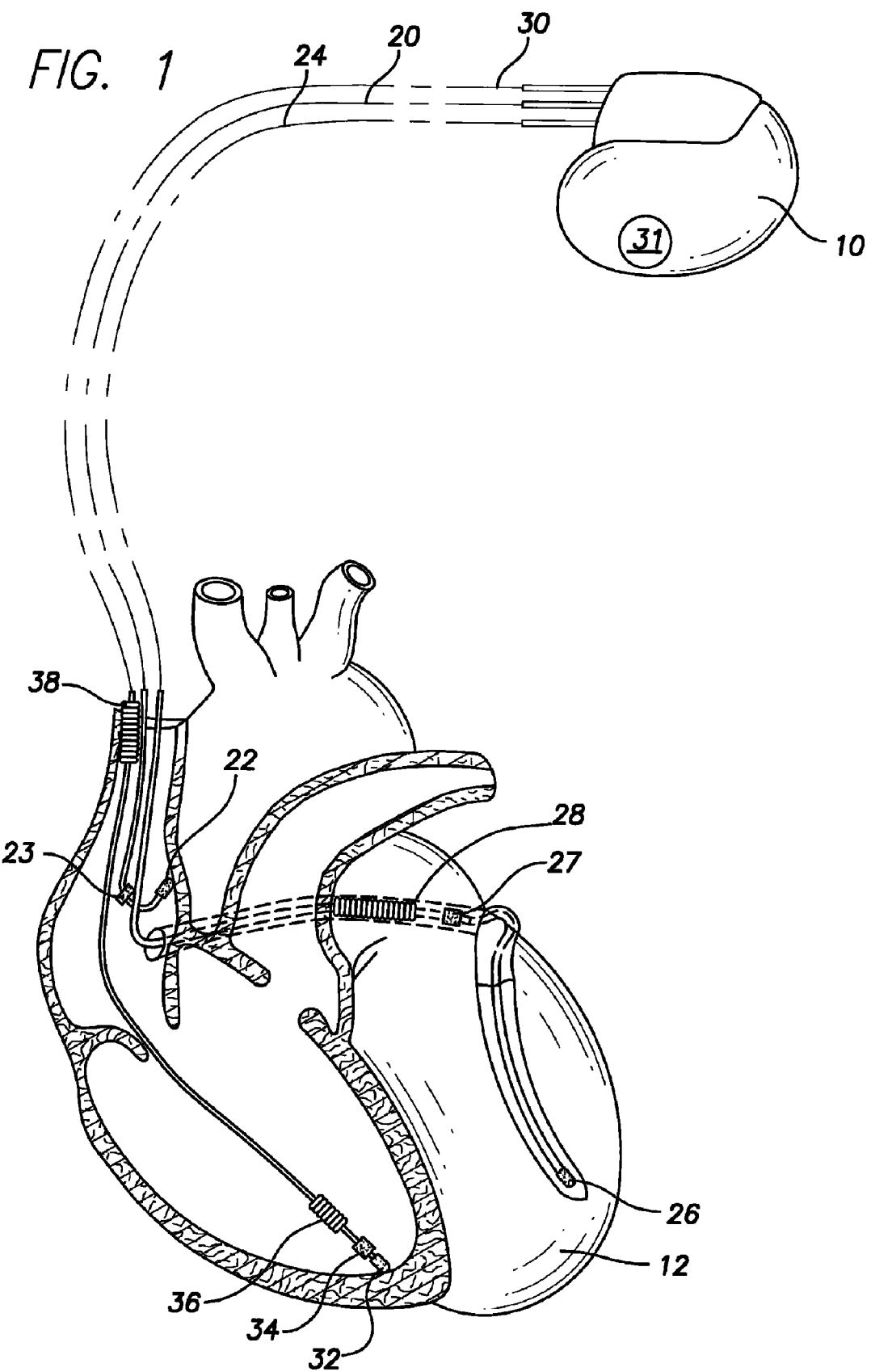
FIG. 1 is a diagram illustrating a stimulation device in electrical communication with a heart of a patient by way of three leads suitable for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode 31 can be provided in proximity to the device can.

Figure 2:
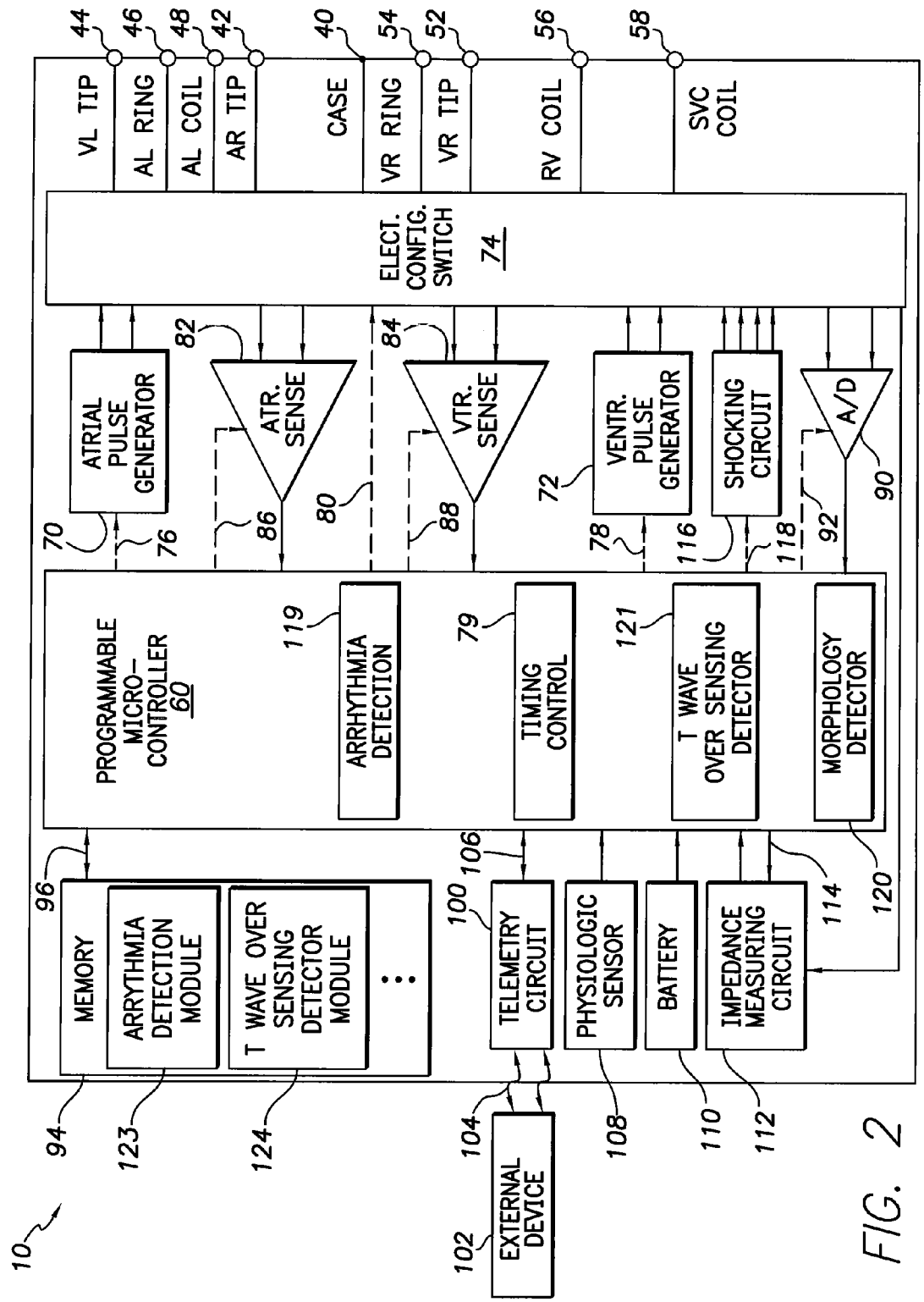
FIG. 2 is a simplified block diagram illustrating a multi-chamber implantable stimulation device capable of treating both fast and slow arrhythmias with stimulation therapy.
Figure 3:
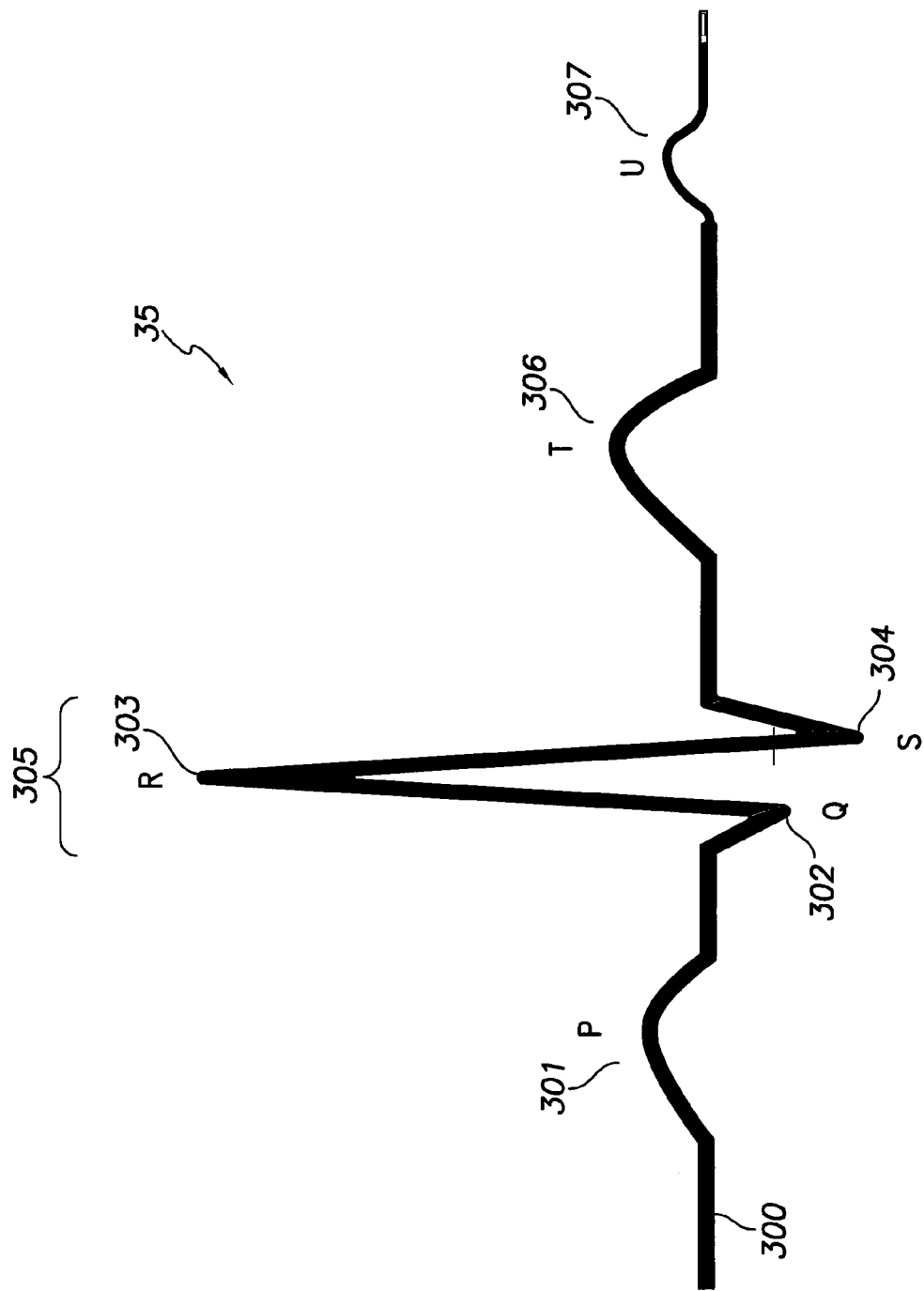
FIG. 3 is an illustration of an idealized electrocardiograph (ECG) trace over a single a cardiac cycle.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, (FIG. 1) for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals).

As such, to achieve right atrial sensing and pacing, the connector includes at least a right atrial tip terminal ($A_R$ TIP) 42 adapted for connection to the atrial tip electrode 22 (FIG. 1) and a right atrial ring ($A_R$ RING) electrode (not shown) adapted for connection to the right atrial ring electrode 23 (FIG. 1). To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26 (FIG. 1), the left atrial tip electrode 27 (FIG. 1), and the left atrial coil electrode 28 (FIG. 1), respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit 122 generates a signal for an additional terminal (not shown) for connection to the vibratory alert electrode 31 (FIG. 1). In one embodiment, the vibratory alert will alert the patient, and then a home monitor can be used to transfer the information associated with the alert from the device 10 to an attending medical professional, who can take the appropriate clinical action.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of the memory. The details of the design and operation of the microcontroller 60 are not critical to the invention. Rather, any suitable microcontroller 60 may be used that carries out the functions described. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20 (FIG. 1), the right ventricular lead 30 (FIG. 1), and/or the coronary sinus lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., as is well known in the art. The switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the coronary sinus lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (ND) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the coronary sinus lead 24 (FIG. 1), and the right ventricular lead 30 (FIG. 1) through the switch 74 to sample cardiac signals across any pair of desired electrodes. The controller 60 controls the data acquisition system via control signals 92.

The microcontroller 60 is further coupled to a memory 94 by a suitable data/address bus 96. The programmable operating parameters used by the microcontroller 60 are stored and modified, as required, in order to customize the operation of the stimulation device 10 to suit the needs of a particular patient. The memory 94 includes software modules, such as an arrhythmia detection module 123 and a T wave oversensing detector module 124, which, when executed by the microcontroller 60, provide the operational functions of the implantable stimulation device 10. Additional operating parameters and code stored on memory 94 define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intra-cardiac electrograms and status information relating to the operation of the device 10 (as contained in the microcontroller 60 or memory 94) to be sent to the external device 102 through an established communication link 104. In one embodiment, the stimulation device 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 is capable of operating at low current drains for long periods of time, and is capable of providing high-current pulses (for capacitor charging) when the patient requires a shock pulse. The battery 110 also has a predictable discharge characteristic so that elective replacement time can be detected. In one embodiment, the device 10 employs lithium/silver vanadium oxide batteries. As further shown in FIG. 2, the device 10 has an impedance measuring circuit 112 enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28 (FIG. 1), the RV coil electrode 36 (FIG. 1), and/or the SVC coil electrode 38 (FIG. 1). As noted above, the housing 40 may function as an active electrode in combination with the RV coil electrode 36 (FIG. 1), or as part of a split electrical vector using the SVC coil electrode 38 (FIG. 1) or the left atrial coil electrode 28 (FIG. 1) (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, the microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an arrhythmia detection control 119 that analyzes the sensed electrical signals to determine whether or not arrhythmia is being experienced. Moreover, the microcontroller 60 includes a T wave oversensing detector 121, which analyzes the sensed R-R intervals by transforming the R-R interval signals into the frequency domain and determining whether any resulting peak and randomness criteria for the dominant frequency meet those criteria indicative of a cardiac episode for which treatment should be administered. The operation of these devices will be described below with reference to the remaining figures.

The remaining figures, flow charts, graphs and other diagrams illustrate the operation and novel features of the stimulation device 10 as configured in accordance with exemplary embodiments of the invention. In the flow chart, the various process steps are summarized in individual "blocks." Such blocks describe specific actions or decisions made or carried out as the process proceeds. Where a microcontroller (or equivalent) is employed, the flow chart provides the basis for a "T wave oversensing program" that may be used by such a microcontroller (or equivalent) to detect T wave oversensing to prevent improper treatment. Those skilled in the art may readily write such a program based on the flow chart and other descriptions presented herein.

Addressing T Wave Oversensing

Figure 4:
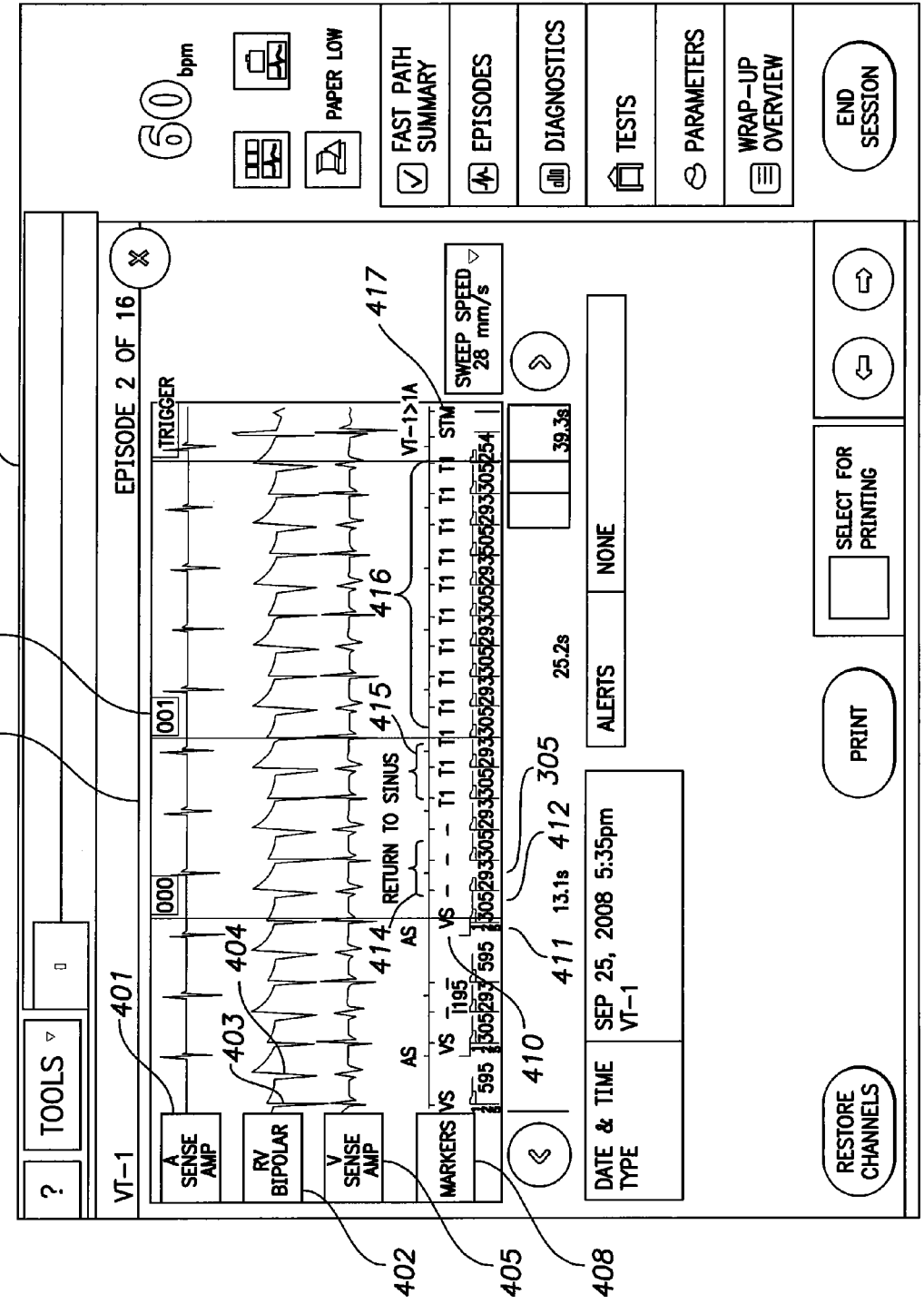
FIG. 4 is a diagram illustrating a display of an ECG recorded by an ICD in which T wave oversensing has triggered delivery of inappropriate treatment.

Turning now to FIG. 4, a diagram is presented that illustrates a display 45 of an ECG recorded by an ICD device 10 in which T wave oversensing has triggered delivery of inappropriate treatment. An ECG read out 400 includes the display of atrial-sensed events from an atrial sense amp 401, ventricular-sensed events from a RV bipolar sensor 402, and processed ventricular-sensed events from a ventricular sense amp 405. The ventricular-sensed events displayed from the RV bipolar sensor 402 illustrate the sensing of R waves, such as R wave 403, and T waves, such as T wave 404. The wider bandwidth of T wave 404 is indicative of the sensed impulse being a T wave. However, as far as the ICD device 10 is concerned, it believes that the sensed T wave 404 is actually another R wave.

The ventricular-sensed events are further processed to provide a narrow bandwidth representation from the ventricular sense amp 405. The signal reproduced by the ventricular sense amp 405 represent an R wave 406 and a T wave 407. The ICD device 10 analyzes the atrial and ventricular events and provides a listing of those analyzed events through a markers section 408. For example, the markers section 408 displays AS 409, which is a sensed and recognized atrial event. Markers section 408 displays VS 410, which is a sensed and recognized ventricular event. The markers section 408 also provides the interval timing between the AS 409 and VS 410 events in location 411 (199 milliseconds (ms)). An interval for each subsequent sensed event is presented for the remainder of the markers section 408, for example at locations 412 (305 ms) and 413 (293 ms). The events detected during the time period 414 are represented as dashes, "-", because the ICD device 10 sensed some kind of ventricular event but was unable to recognize what type of event the signal represents. Having sensed multiple ventricular events in the VS 410 and through the time period 414, the next ventricular events sensed during the time period 415 are characterized as "T1" ventricular events, i.e., ventricular events that are classified within the tachycardial level 1 range.

Because the ICD device 10 does not expect to sense T waves, it interprets or assumes that all of the ventricular events sensed from the VS 410 through the time periods 414 and 415, as R wave events. These incorrectly sensed "R" waves occur at such short interval periods, the ICD device 10 assumes the patient is experiencing ventricular tachycardia, hence, the classification in time period 415 as T1 events. After these six closely-spaced ventricular events are sensed in time periods 414 and 415, the ICD device 10 enters the DDI mode 418 during which the ICD device 10 prepares to administer treatment for the improperly diagnosed tachycardia. The ICD device 10 continues to sense T1 ventricular events over the DDI time period 416, as shown in the markers section 408. The continuing number of such sensed ventricular events allows the ICD device 10 to incorrectly detect a treatable cardiac episode and, at time 417, the ICD device 10 issues an electrical shock treatment to the patient, even though the patient is experiencing a normal sinus rhythm.

Figure 5:
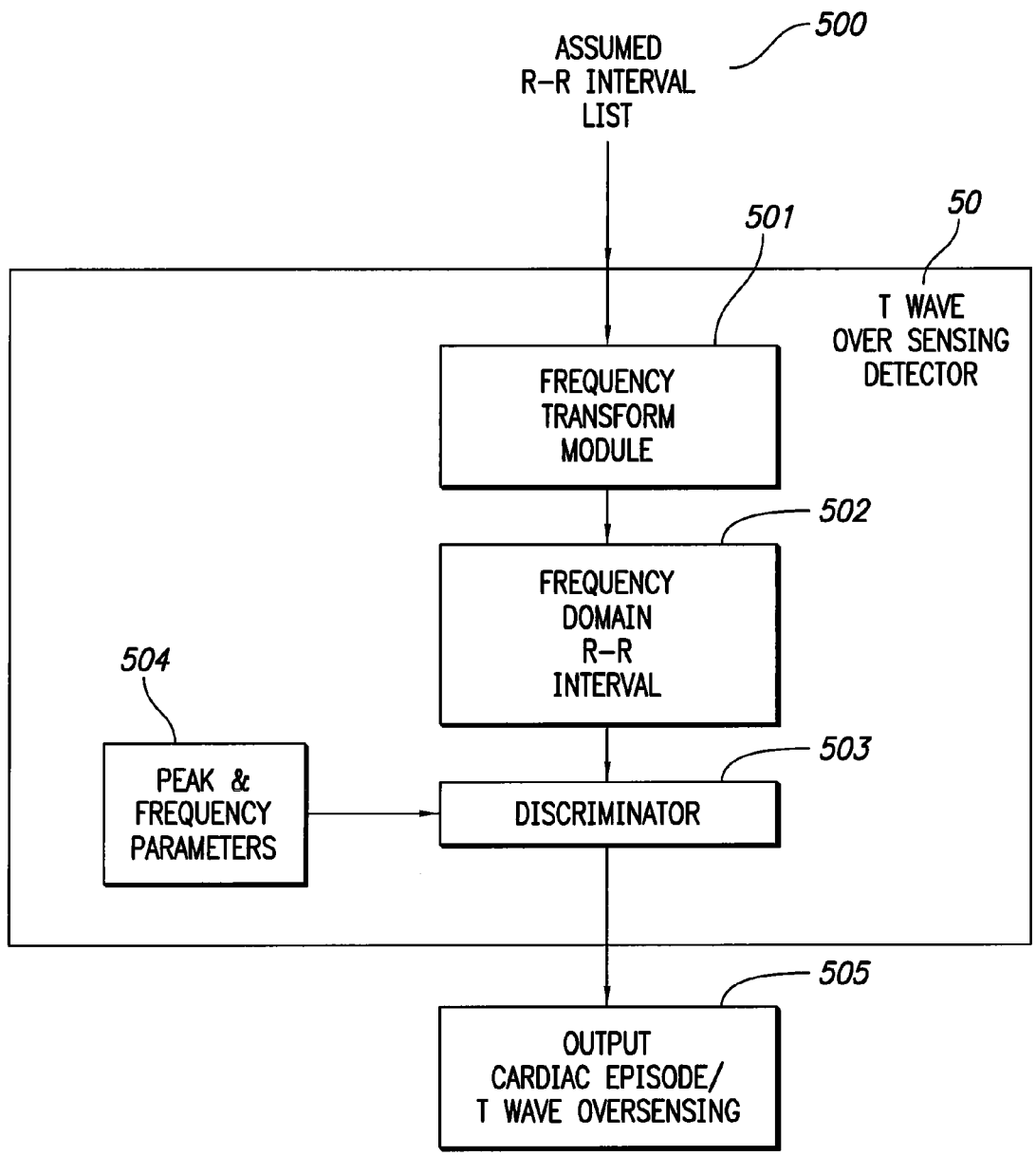
FIG. 5 is a block diagram illustrating a T wave oversensing detector as configured according to one embodiment of the present teachings.

FIG. 5 is a block diagram illustrating T wave oversensing detector 50 as configured according to one embodiment of the present teachings. T wave oversensing detector 50 receives the assumed R-R interval list 500 as sensed by stimulation device 10. The assumed R-R interval list 500 comprises a list of the intervals detected between each R wave in a particular analysis window. The assumed R-R interval list 500 is processed by a frequency transform module 501 in order to transform the list of intervals into its equivalent frequency domain R-R interval 502. The frequency transform module 501 may use various methods for transforming the assumed R-R interval list 500 into the frequency domain R-R interval 502, such as by using a fast Fourier transform (FFT), a discrete Fourier transform (DFT), a Laplace transform, a discrete wavelet transform (DWT), and the like.

The frequency domain R-R interval 502 is then processed at a discriminator 503 which analyzes the peaks and dominant frequencies found in the frequency domain R-R interval 502. The discriminator 503 uses a database of parameters in a peak and frequency parameters database 504 in order to define the randomness of the peaks and what frequencies relate to the threshold points between actual ventricular arrhythmias and probable oversensing of T waves. The discriminator 503 produces output 505, which indicates either that a cardiac episode is taking place or that the detected arrhythmia is, in fact, T wave oversensing. This output 505 is used by the stimulation device 10 (FIG. 1) to decide whether treatment is warranted based on what it has sensed as an arrhythmia.

Figure 6:
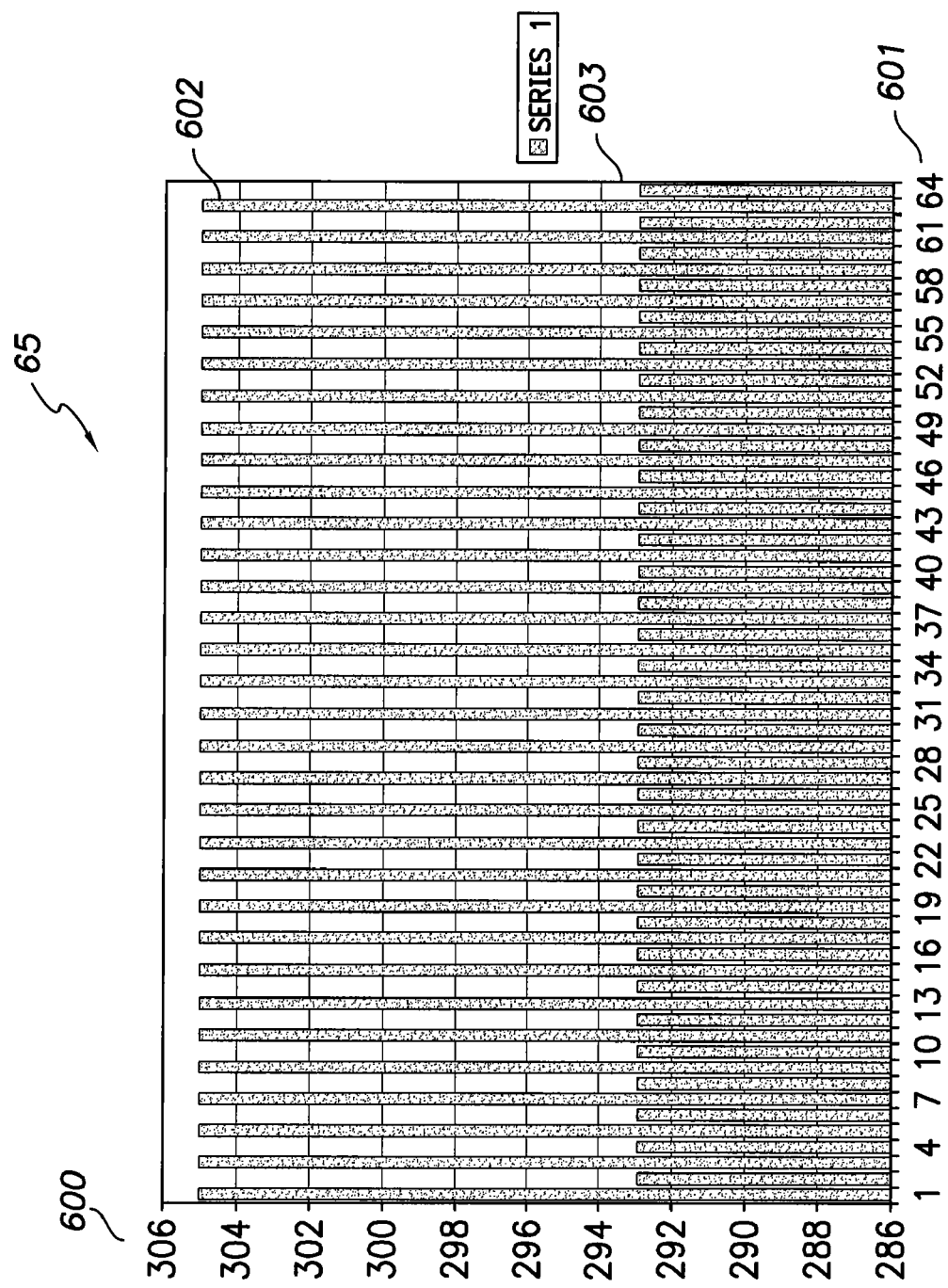
FIG. 6 is a chart illustrating an R-R interval list presenting with constant T wave oversensing.

FIG. 6 is a chart illustrating an assumed R-R interval list 65 presenting with constant T wave oversensing. The assumed R-R interval list 65 is defined by the interval time 600, in milliseconds, on the y-axis, and the sample number 601, on the x-axis. With reference to FIG. 4, the time intervals, such as the intervals at the locations 412 and 413, reflect an alternating sequence between 293 ms to 305 ms to 293 ms to 305 ms, and so on. Each bar on the assumed R-R interval list 65 similarly reflects a first interval, such as interval 602, at 305 ms, and a subsequent interval, such as interval 603, at 293 ms. Because the assumed R-R interval list 65 illustrates this alternating interval between 305 ms and 293 ms throughout the entire sample, an ICD device 10 sensing these alternating intervals could determine that the patient was experiencing ventricular tachycardia.

Figure 7:
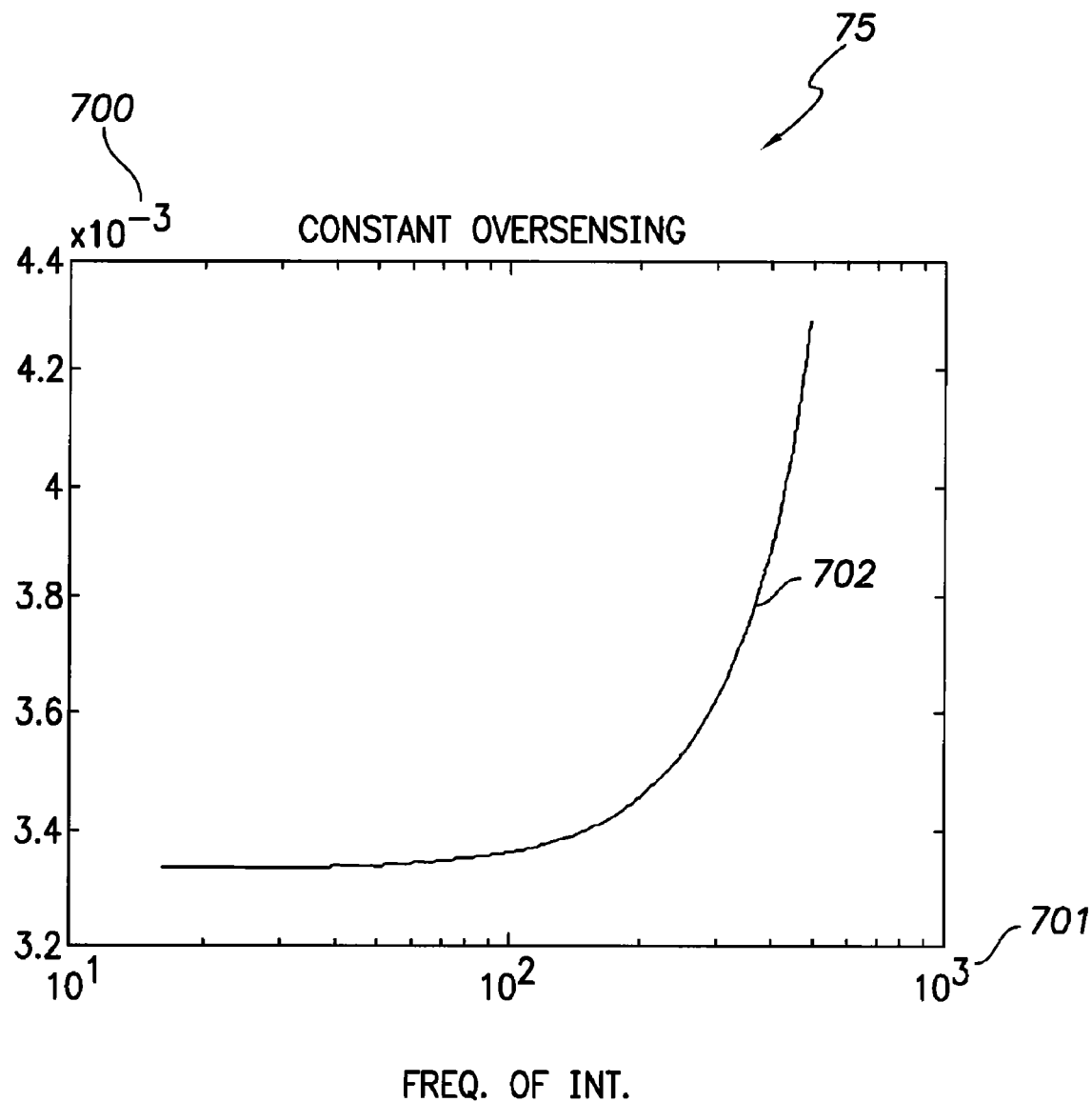
FIG. 7 is a chart illustrating a frequency domain R-R interval after processing by an ICD configured according to one embodiment of the present teachings.

FIG. 7 is a chart illustrating a frequency domain R-R interval 75 after processing by an ICD device 10 configured according to one embodiment of the present teachings. The frequency domain R-R interval 75 is defined by power 700, on the y-axis, and frequency 701, on the x-axis. The frequency domain R-R interval 75 is the result of the ICD device 10 processing the R-R interval list 65 using a frequency transform. The ICD device 10 analyzes the frequency domain R-R interval 75 to determine whether the sensed R-R intervals reflect a cardiac episode or merely T wave oversensing. The plot 702 of the frequency domain R-R interval 75 reflects a low power level at lower frequencies that exponentially increases toward infinity power at the higher frequencies. Therefore, the dominant frequency in plot 702 arises at the highest power level, which is indicative of T wave oversensing.

It should be noted that when transforming the assumed R-R interval list 65 into its frequency domain equivalent, the frequency domain R-R interval 75, using an FFT, the results include a real part and an imaginary part. The plot of the frequency domain R-R interval 75, as illustrated in FIG. 7, is generated by taking the square root of the sum of the squares of the real and imaginary parts of the FFT results. The various representative embodiments of the present teachings are not limited solely to using an FFT transform. Other frequency domain transforms and corresponding graphing techniques may also be used.

Figure 8:
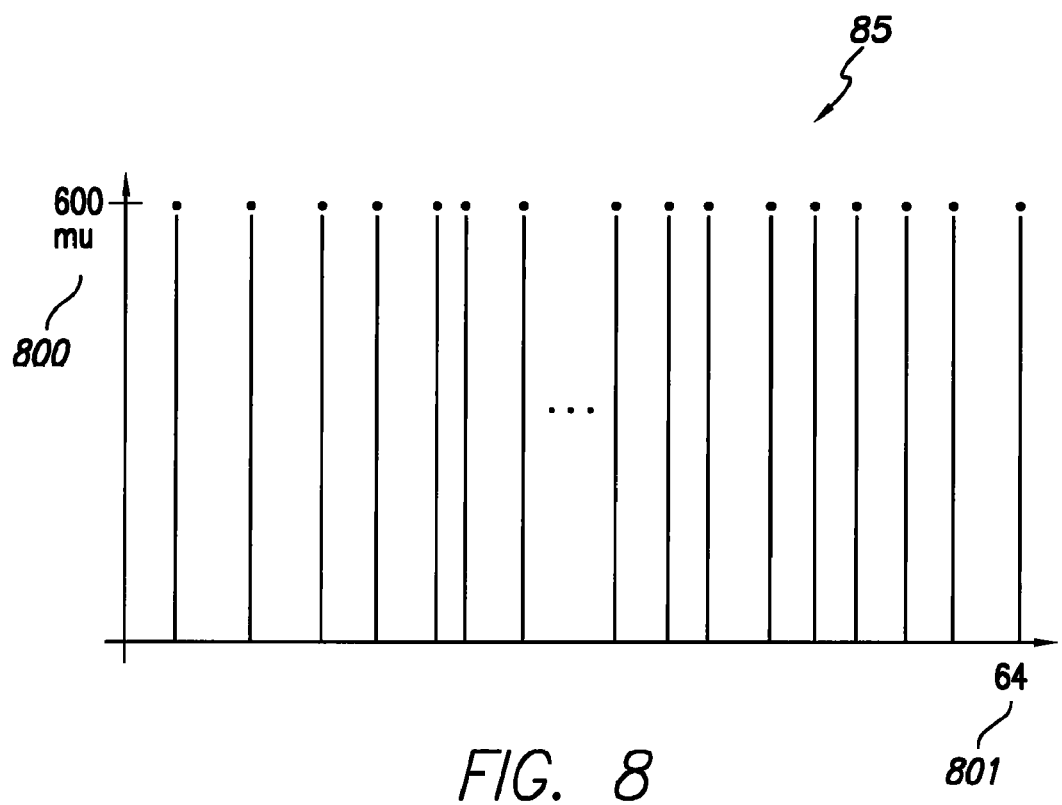
FIG. 8 is a chart illustrating an R-R interval list presenting with no T wave oversensing.
Figure 9A:
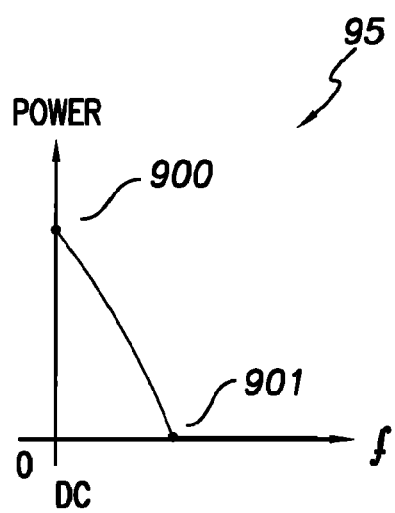
FIG. 9A is a chart illustrating a frequency domain R-R interval after processing by an ICD configured according to one embodiment of the present teachings.
Figure 9B:
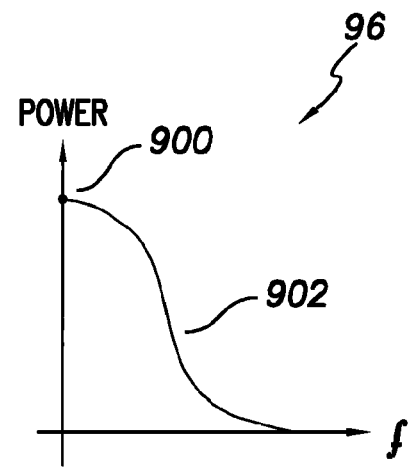
FIG. 9B is a chart illustrating a frequency domain R-R interval after processing by an ICD configured according to one embodiment of the present teachings.

FIG. 8 is a chart illustrating an R-R interval list 85 presenting with no T wave oversensing. The R-R interval list 85 is defined by the interval time 800, in milliseconds, on the y-axis, and the sample number 801, on the x-axis. A steady state heartbeat will usually result in constant or near-constant R-R intervals. The intervals of the R-R interval list 85 measure at 600 ms. When a list of these constant intervals is processed into its frequency domain equivalent, the dominant frequency will usually have the highest power at a zero frequency, i.e., 0 Hz. FIG. 9A is a chart illustrating a frequency domain R-R interval 95 after processing by an ICD device 10 configured according to one embodiment of the present teachings. The dominant frequency 900 shows highest power at 0 Hz. As the frequency increases in this steady state case, the power decreases linearly (in a sample without respiration) until no power 901 is generated. FIG. 9B is a chart illustrating a frequency domain R-R interval 96 after processing by an ICD device 10 configured according to one embodiment of the present teachings. The dominant frequency 900 again shows highest power at 0 Hz. However, as the frequency increases in this steady state case, the power decays at a nonlinear rate 902, in this sample that includes respiration. The process of respiration changes the pressure in the chest cavity which has the effect of slightly lowering and/or raising the heartbeat around the respirations.

Plot 702 of the frequency domain R-R interval 75 (FIG. 7) illustrates a result that is substantially abnormal from what would be expected from steady state R-R intervals, as illustrated in FIGS. 9A and 9B. Thus, the discriminator 503 (FIG. 5) determines that the frequency domain R-R interval 75 represents a T wave oversensing situation. It would then signal the ICD device 10 that treatment is not appropriate.

It should be noted that, while ICD devices configured according to various embodiments of the present teachings perform to accurately detect T wave oversensing in a situation where T wave oversensing is constant or near constant, existing methods, such as the ASC and Bigeminal avoidance, may also accurately detect constant or near constant T wave oversensing and prevent inappropriate treatment. However, this detection of constant oversensing can be limited in the existing methods by various timers, such as maximum time to therapy (MTT) timers and maximum time to diagnosis (MTD) timers. If a Bigeminally estimated T wave oversensing period extends for such a period that the heartbeat would be measured in a potential Tach B (160-200 beats per minute (bpm)) or FIB (>200 bpm) diagnosis, preventing treatment through Bigeminal avoidance could be dangerous if the determination of Bigeminy is, in fact, incorrect. The MTT and MTD timers essentially stop the Bigeminal avoidance and trigger administration of treatment if it is sustained over a predetermined period of time. Thus, the various embodiments of the present teachings may be used in combination with existing ASC and Bigeminal avoidance techniques in order to detect T wave oversensing even when existing ASC or Bigeminal avoidance techniques either cannot detect intermittent over sensed T waves or when Bigeminal avoidance techniques are stopped for safety when used with MTT and MTD timers.

Moreover, the current methods have been found lacking in detecting T wave oversensing when the oversensing is intermittent. In contrast, the various embodiments of the present teachings are unaffected by intermittent oversensing and can accurately detect intermittent T wave oversensing.

Figure 10:
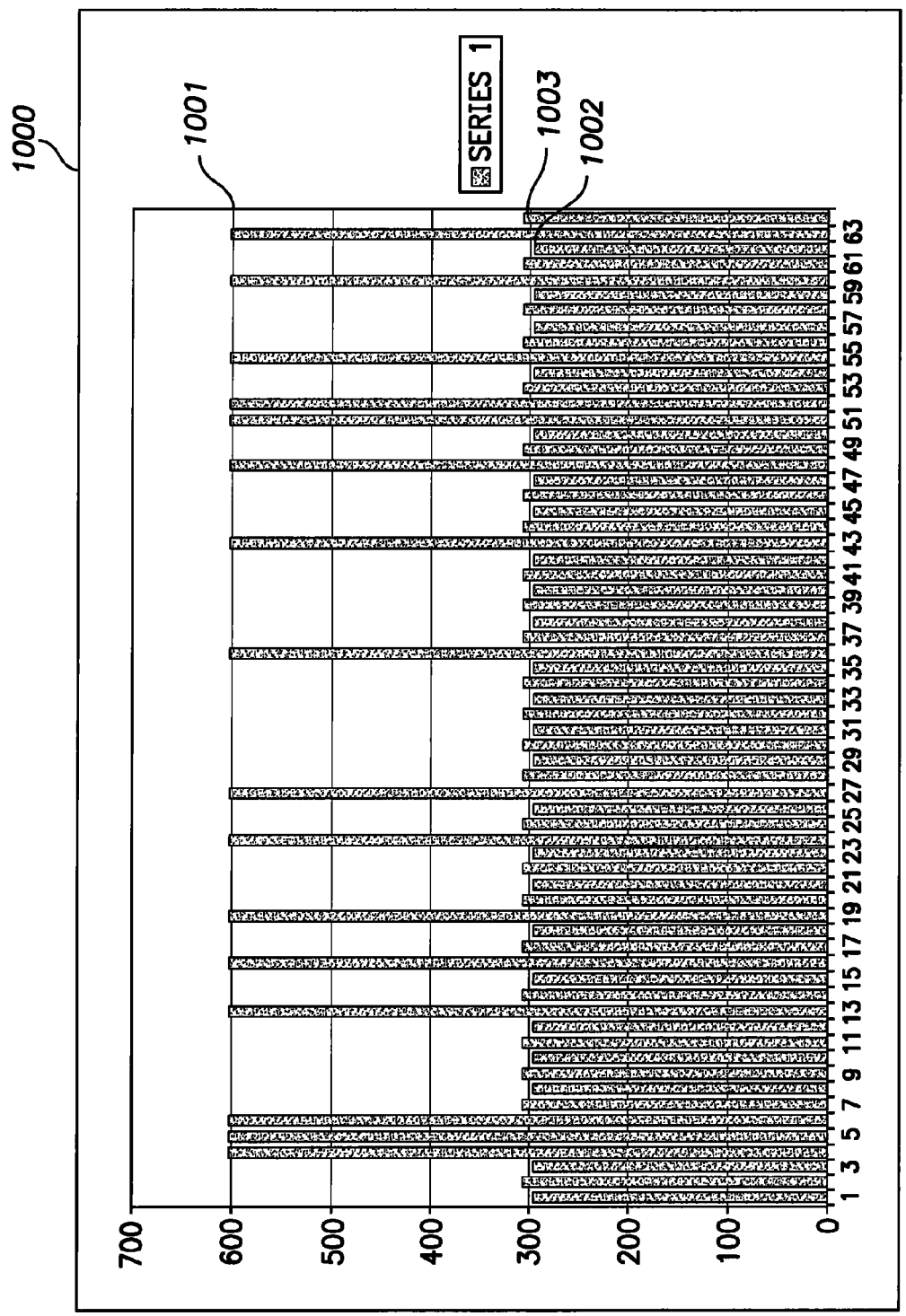
FIG. 10 is a chart illustrating an R-R interval list presenting with intermittent T wave oversensing.
Figure 11:
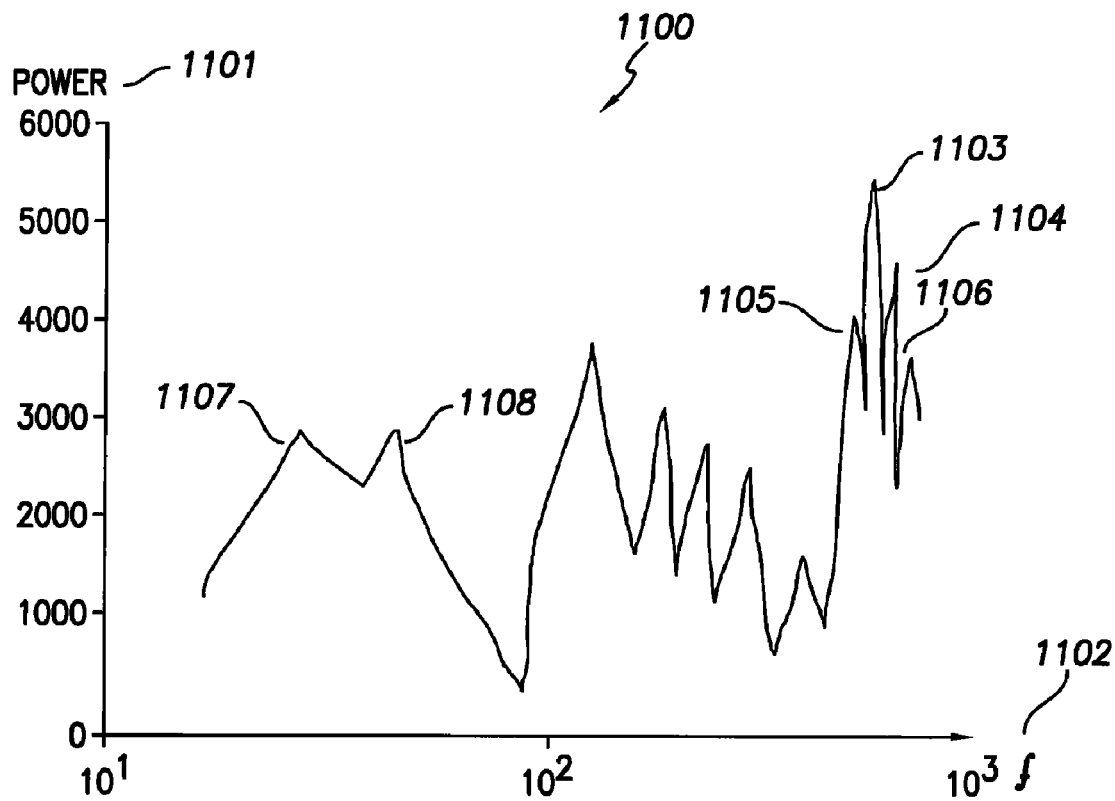
FIG. 11 is a chart illustrating a frequency domain R-R interval after processing by an ICD configured according to one embodiment of the present teachings.

FIG. 10 is a chart illustrating an R-R interval list 1000 presenting with intermittent T wave oversensing. The oversensing is illustrated by the intervals of approximately 600 ms (interval 1000) in the complete cardiac cycles along with the intermittent over sensed intervals of approximately 293 ms (interval 1002) and approximately 305 ms (interval 1003). FIG. 11 is a chart illustrating a frequency domain R-R interval 1100 after processing by an ICD device 10 configured according to one embodiment of the present teachings. The frequency domain R-R interval 1100 is defined by power 1101, on the y-axis, and frequency 1102, on the x-axis. The frequency domain R-R interval 1100 results in multiple power peaks over a wide frequency range. Again, the frequency domain R-R interval 1100 appears substantially different from a typical frequency domain R-R interval of a steady state heartbeat. A discriminator, such as the discriminator 503 (FIG. 5), analyzes the peaks and frequencies to determine whether or not T wave oversensing has occurred. For example, discriminator 503 determines that the dominant frequency 1103 occurs at a very high power and frequency. Moreover, local peaks 1104-1106, having high power and frequency, occur randomly around the dominant frequency 1103. The randomness in which the local peaks 1104-1106 occur around dominant frequency 1103 indicates that T wave oversensing is occurring within this assumed R-R interval list 1000.

Additionally, the lower frequency peaks 1107 and 1108 each have the same or almost the same power levels. Multiple frequency peaks having the same or almost the same power levels is an indication of intermittent T wave oversensing. Thus, by analyzing the randomness of dominant frequency 1103 and the local peaks 1104-1106 and the power levels of lower frequency peaks 1107 and 1108, the discriminator 503 (FIG. 5) may determine that T wave oversensing is occurring.

Figure 12:
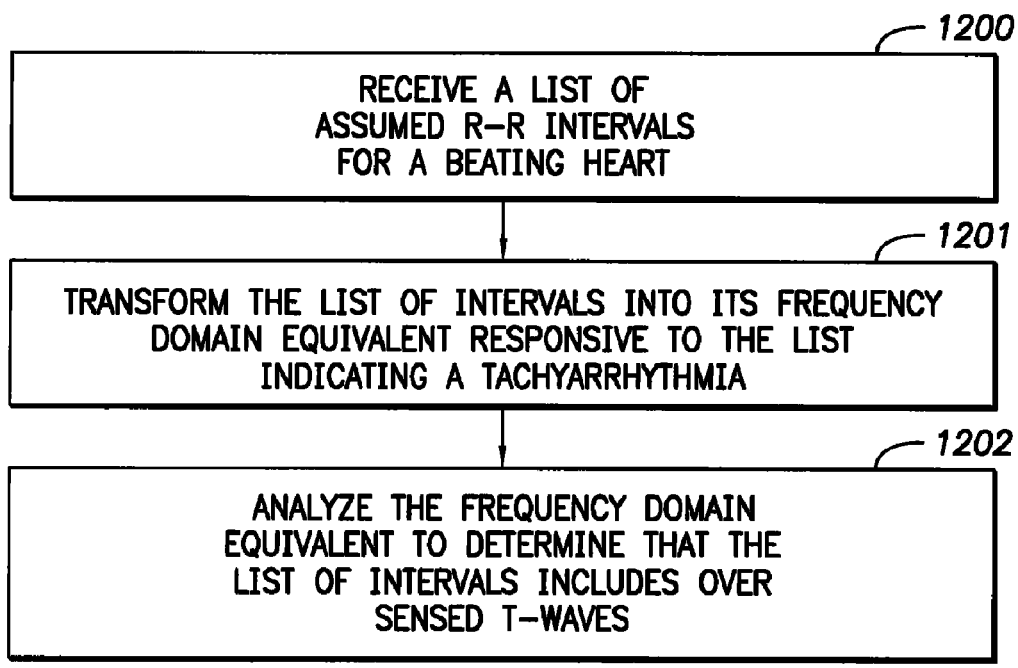
FIG. 12 flowchart illustrating functional blocks providing T wave over sense detection in an ICD device configured according to one embodiment of the present teachings.

FIG. 12 is a flowchart illustrating functional blocks providing T wave over sense detection in an ICD device 10 configured according to one embodiment of the present teachings. In functional block 1200, a list of assumed R-R intervals is received for a beating heart. The list of assumed R-R intervals is transformed into its frequency domain equivalent, in functional block 1201, responsive to the list indicating a tachyarrhythmia. The frequency domain equivalent is analyzed to determine that the list of assumed R-R intervals includes over sensed T waves.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine or computer readable medium tangibly embodying instructions that may be in a form implantable or coupled to an ICD device may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored.

The machine or computer readable medium that stores the software code defining the methodologies and functions described herein includes physical computer storage media. A storage medium may be any available medium that can be accessed by the processor of an ICD device. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed:

1. In an implantable medical device, a method for determining T wave oversensing in cardiac electrical signals, the method comprising:
   receiving, by the implantable medical device, a list of assumed R-R intervals for a beating heart;
   transforming, by the implantable medical device, the list of assumed R-R intervals into a frequency domain equivalent, responsive to the list of assumed R-R intervals indicating a tachyarrhythmia; and
   analyzing, by the implantable medical device, the frequency domain equivalent to determine whether the list of assumed R-R intervals includes over sensed T waves.

2. The method of claim 1 wherein the cardiac electrical signals are sensed in an implantable cardioverter/defibrillator (ICD) device, the method further comprising:
   blocking treatment from the ICD device responsive to the determination of the over sensed T waves.

3. The method of claim 1 wherein the analyzing comprises:
   analyzing a power level of peaks detected in the frequency domain equivalent.

4. The method of claim 3 wherein inclusion of over sensed T waves is determined based on said analyzing resulting in a plurality of low frequency peaks having substantially the same said power level.

5. The method of claim 1 wherein the analyzing comprises:
   analyzing a randomness of a plurality of local peaks detected in the frequency domain equivalent.

6. The method of claim 5 wherein inclusion of over sensed T waves is determined based on said analyzing resulting in a high value of said randomness occurring in said plurality of local peaks at a higher frequency in the frequency domain equivalent.

7. The method of claim 1 wherein inclusion of the over sensed T waves is determined by discovery of at least two peaks having a same power level in the frequency domain equivalent.

8. The method of claim 1 further comprising:
   sensing for wave deflections in a measurement of electrical impulses emitted from the beating heart, wherein the wave deflections are assumed to be R wave deflections;
   measuring an interval between each sensed wave deflection; and
   generating the list of assumed R-R intervals using each of the measured intervals.

9. The method of claim 1 wherein the transforming comprising:
   processing the list of assumed R-R intervals using one of:
      a fast Fourier transform (FFT);
      a discrete Fourier transform (DFT);
      a Laplace transform; and
      a discrete wavelet transform (DWT).

10. A system for detecting T wave oversensing in cardiac electrical signals comprising:
    means for receiving a list of assumed R-R intervals for a beating heart;
    means, operable in response to the list of assumed R-R intervals indicating a tachyarrhythmia, for transforming the list of assumed R-R intervals into a frequency domain equivalent; and
    means for analyzing the frequency domain equivalent to determine whether the list of assumed R-R intervals includes over sensed T waves.

11. The system of claim 1 wherein the cardiac electrical signals are sensed in an implantable cardioverter/defibrillator (ICD) device, the system further comprising:
    means for blocking treatment from the ICD device responsive to the determination of the over sensed T waves.

12. The system of claim 1 wherein the means for analyzing the frequency domain equivalent comprises means for analyzing a power level of peaks detected in the frequency domain equivalent.

13. The system of claim 12 wherein inclusion of the over sensed T waves is determined based on said means for analyzing resulting in a plurality of low frequency peaks having substantially the same said power level.

14. The system of claim 1 wherein the means for analyzing comprises means for analyzing a randomness of a plurality of local peaks detected in the frequency domain equivalent.

15. The system of claim 14 wherein inclusion of the over sensed T waves is determined based on said means for analyzing resulting in a high value of said randomness occurring in said plurality of local peaks at a higher frequency in the frequency domain equivalent.

16. The system of claim 1 wherein inclusion of the over sensed T waves is detected when at least two peaks have a same power level in the frequency domain equivalent.

17. The system of claim 1 further comprising:
means for sensing wave deflections in a measurement of electrical impulses emitted from the beating heart, wherein the wave deflections are assumed to be R wave deflections;
means for measuring an interval between each sensed wave deflection; and
means for generating the list of assumed R-R intervals using each of the measured intervals.

18. The system of claim 1 wherein the means for transforming comprises:
means for processing the list of assumed R-R intervals using one of:
a fast Fourier transform (FFT);
a discrete Fourier transform (DFT);
a Laplace transform; and
a discrete wavelet transform (DWT).

* * * * *